(12) United States Patent
Garms et al.

(10) Patent No.: US 7,492,860 B2
(45) Date of Patent: Feb. 17, 2009

(54) APPARATUS AND METHOD FOR CONTROLLING START AND STOP OPERATIONS OF A COMPUTED TOMOGRAPHY IMAGING SYSTEM

(75) Inventors: Walter Garms, Berkeley, CA (US); Pierfrancesco Landolfi, Newark, CA (US)

(73) Assignee: GE Security, Inc., Bradenton, FL (US)

( * ) Notice: Subject to any disclaimer, the term of this patent is extended or adjusted under 35 U.S.C. 154(b) by 277 days.

(21) Appl. No.: 11/397,792

(22) Filed: Apr. 4, 2006

(65) Prior Publication Data

US 2007/0230657 A1   Oct. 4, 2007

(51) Int. Cl.
G01N 23/04 (2006.01)
G01N 23/00 (2006.01)

(52) U.S. Cl. ............................. 378/57; 378/4
(58) Field of Classification Search ................ 378/4, 378/19, 20, 57, 62, 68, 69, 98.8, 208, 209
See application file for complete search history.

(56) References Cited

U.S. PATENT DOCUMENTS

| | | | |
|---|---|---|---|
| 5,123,523 A | 6/1992 | Langlois | 198/844 |
| 5,182,764 A | 1/1993 | Peschmann | 378/57 |
| 5,367,552 A | 11/1994 | Peschmann | 378/57 |
| 5,796,802 A * | 8/1998 | Gordon | 378/8 |
| 5,960,056 A | 9/1999 | Lai | 378/4 |
| 6,647,084 B1 | 11/2003 | Hsieh | 378/4 |
| 6,947,584 B1 | 9/2005 | Avila | 382/131 |
| 6,953,935 B1 | 10/2005 | Hoffman | 250/370.13 |
| 7,333,589 B2 * | 2/2008 | Ellenbogen et al. | 378/57 |
| 2003/0215054 A1 * | 11/2003 | Fenkart et al. | 378/57 |
| 2006/0104414 A1 * | 5/2006 | Mayo | 378/57 |

* cited by examiner

*Primary Examiner*—Irakli Kiknadze
(74) *Attorney, Agent, or Firm*—Eugene Hyun, Esq.; Armstrong Teasdale LLP (57) ABSTRACT

An apparatus and method for scanning an object with a helical CT scanner, the method comprising: acquiring an amount of data corresponding to the object that is scanned by the CT scanner, wherein the amount of data is generated by an x-ray source that projects a fan beam of x-rays toward a detector array on an opposite side of a gantry of the CT scanner, the fan beam being generated at multiple x-ray source positions as the x-ray source is rotated about the object as the object passes through an opening in the gantry disposed about a conveyor for moving the object through the opening; monitoring a position of the conveyor as the object passes through the opening in the gantry; determining if the conveyor has been stationary for more than one rotation of the gantry and discarding redundant data after one rotation, optionally turning off the x-ray tube if the conveyor has been stationary for more than one gantry rotation, and if so preventing the conveyor from moving again until the tube is turned on and is stable, inputting the position of the conveyor at each x-ray source position into a reconstruction algorithm; and presenting an image of the object.

31 Claims, 5 Drawing Sheets

APPARATUS AND METHOD FOR CONTROLLING START AND STOP OPERATIONS OF A COMPUTED TOMOGRAPHY IMAGING SYSTEM

BACKGROUND

This present invention relates to methods and apparatus for controlling a computed tomography imaging system. More particularly, exemplary embodiments of the present invention are related to methods and apparatus for operating a computed tomography (CT) imaging system in conjunction with a system of conveyors. Such a system may be used for security screening or non-destructive testing.

X-ray based security systems are deployed world-wide in airports to detect explosives, weapons, contraband, or other prohibited items in carry-on and checked baggage. Currently, most carry-on inspection systems are line scanners, which produce a transmission image (also known as scan projection or SP image) of a bag. More advanced CT systems are often used for checked baggage inspection. In many such systems, bags are transported into and out of the scanner by means of a system of conveyor belts.

Line scan systems utilize a scan projection (SP) image for presentation to the operator. In line scan systems, scan projection images are created by moving an object under a fan beam of x-rays from a stationary x-ray source. X-ray intensities, after being attenuated by the object being scanned, are measured by an array of detectors. The x-ray intensity data is converted through a process called normalization so that each pixel represents approximately the total mass traversed by the ray.

In computed tomography (CT) imaging systems, an x-ray source projects a fan-shaped beam, which is collimated to lie within an X-Y plane of a Cartesian coordinate system and generally referred to as an "imaging plane". The x-ray beam passes through an object being imaged. The beam, after being attenuated by the object, impinges upon an array of radiation detectors. The intensity of the attenuated radiation beam received at the detector array is dependent upon the attenuation of the x-ray beam by the object. Each detector element of the array produces a separate electrical signal that is a measurement of the beam intensity at each detector location. The intensity measurements from all the detectors are acquired separately to produce a transmission profile.

In third generation CT systems, the x-ray source and the detector array are rotated around the object to be imaged such that the angle at which the x-ray fan beam intersects the object constantly changes. A group of x-ray attenuation measurements (e.g., projection data), from the detector array at one gantry angle is referred to as a "view". A "scan" of the object comprises a set of views made at different gantry angles, or view angles, during one revolution of the x-ray source and detector about the object or patient being imaged. A cross sectional image of the scanned plane can be reconstructed using well-known tomographic reconstruction algorithms such as direct Fourrier or filtered back projection methods.

Many modern CT systems are helical scanners (also known as spiral scanners), in which the scanned object is continually moved while the projection data is being acquired. The path of the X-Ray source describes a helix with respect to the scanned object. Most helical scanners have multiple rows of detectors, and the x-ray fan is collimated into a cone to illuminate the entire array of detectors. The angle between the x-ray source and the first and last detector rows is referred to as the "cone angle".

The entire volume scanned by the helical scanner can be reconstructed using well-known tomographic reconstruction algorithms such as direct Fourrier or filtered back projection methods, and more exact methods described by Feldkamp and Katsevich. The advantage of a helical scanner is that much more of the object is scanned with each rotation of the x-ray source, thereby decreasing the time required to acquire sufficient data to reconstruct the scanned volume. For medical scanners this means that the patient must remain motionless for less time; for luggage scanners this means that more bags can be scanned per hour.

A CT system for checked baggage or carry-on items may be receiving objects (i.e., luggage) that need to be scanned from a series of conveyor belts, each of which provides an input and an output to the CT system. Moreover, the CT system itself will also have an independent conveyor that operates in conjunction with the output and input conveyors. Most conveyor systems at airports have a series of conveyors, each of which is configured to start, stop, slow down, or accelerate in conjunction with specific requirements of perhaps another single segment of the conveyor. For example, and when an output belt or slide of a single segment of a system is overloaded with luggage that has not been removed that segment will be stopped until the "log jam" is removed. This segment can no longer accept another bag, so if there is a bag on the preceding conveyor, the preceding conveyor must also be stopped, then the conveyor before that one must be stopped, and so forth, until perhaps the entire conveyor system has been stopped. This process is known as a dieback. When the original log jam has been cleared, each conveyor will start in sequence when the conveyor after it is ready to receive a bag.

A CT scanning system and in particular, a helical scanning system is typically configured to utilize reconstruction algorithms that are based upon a constant velocity of the item being passed through a gantry opening of the CT scanner. In other words, reconstruction algorithms that are based upon constant belt velocities will know exactly how much of the object as passed through the scanner after the x-ray source has made one complete revolution about the gantry as the object has passed therethrough. For example, each successive view from a particular x-ray source position along the gantry will correspond to a regular or constant interval and thus, the control algorithm of the scanning system will be written accordingly. As used herein, view refers to a particular location of the x-ray source along a path of rotation, which surrounds an opening of the CT scanning system through which the object is passed and scanned.

Accordingly, and when the CT scanning system is used in a conveyor system that must decelerate and stop, and then restart, this will mean that views (as defined herein) are not taken at regular intervals in the direction of belt movement, and standard spiral interpolation as is known in the related arts cannot be used. It is impractical to back up and restart a belt in a system of conveyors unless additional queuing conveyors are provided on both ends of the scanner. In addition, and if the conveyor belt is stopped for any length of time, a large amount of data will be acquired (e.g., the x-ray source will continue to rotate about the object and accumulate data). The data acquired after the belt stops and the CT source has made one complete revolution at the stopped position is redundant. The amount of redundant data acquired may become too large to save in an appropriately fast storage medium. Moreover, and if the conveyor belt is stopped for an extended time, the scanner may impart an unnecessary amount of radiation on the object being scanned. In order to ensure that the belt speed remains constant during the acquisition of a bag, CT scanners of the prior art must employ a conveyor system such that the entire bag can move through the CT gantry without stopping. Such a conveyor system requires longer or additional belt segments, increasing the overall size of the system. The conveyor system may also require greater spacing between bags, thereby reducing the number of bags that can be scanner per hour.

Accordingly, it is desirable to provide an apparatus and method for continuous data acquisition of an object being scanned when the conveyor belt runs at various speeds, or stops, as the object is being passed through the CT scanner.

BRIEF DESCRIPTION OF THE INVENTION

An apparatus and method for scanning an object with a CT scanner wherein a conveyor of the CT scanner operates at variable speed during an object scan. In accordance with exemplary embodiments of the present invention a conveyor controller is provided which can determine the position of the conveyor at all times using a servo controller, encoder or equivalent device. Views of an object are captured from x-ray source positions, and for each view the conveyor position is provided to a reconstruction algorithm of the CT scanner. The distance of conveyor or object travel between views may be variable or zero. The reconstruction algorithm will utilize variable interpolation in order to reconstruct the data for a projection image.

Moreover, and if the conveyor has stopped for more than one gantry rotation of the x-ray source, the redundant data is no longer stored, or the data is stored in place of the redundant data from the previous rotations. The control system of an exemplary embodiment will detect when the belt starts moving again, and subsequent data is then stored at an appropriate location.

In an alternative implementation the x-ray source may be turned off while data is not being acquired (e.g., extended periods of belt shut down) and in this embodiment an apparatus and method for preventing the belt from moving again until the tube has been turned on and stabilized is provided.

Accordingly, and in one embodiment a method of scanning an object with a CT scanner is provided. The method comprising: acquiring an amount of data corresponding to an object that is scanned by the CT scanner, wherein the amount of data is generated by an x-ray source that projects a fan beam of x-rays toward a detector array on an opposite side of a gantry of the CT scanner, the fan beam being generated at multiple x-ray source positions as the x-ray source is rotated about the object as the object passes through an opening in the gantry disposed about a conveyor for moving the object through the opening; monitoring a position of the conveyor as the object passes through the opening in the gantry; inputting the position of the conveyor at each x-ray source position into a reconstruction algorithm; and presenting an image of the object.

A storage medium encoded with a machine-readable computer program code, the storage medium including instructions for causing a computer to implement a method for scanning an object with a CT scanner, the method comprising: acquiring an amount of data corresponding to the object that is scanned by the CT scanner, wherein the amount of data is generated by an x-ray source that projects a fan beam of x-rays toward a detector array on the opposite side of a gantry of the CT scanner, the fan beam being generated at multiple x-ray source positions as the x-ray source is rotated about the object as the object passes through an opening in the gantry disposed about a conveyor for moving the object through the opening; monitoring a position of the conveyor as the object passes through the opening in the gantry; inputting the position of the conveyor at each x-ray source position into a reconstruction algorithm; and presenting an image of the object.

A computed tomography system for scanning items, the system comprising: a computed tomography scanner, configured to produce x-ray projection data as an object is passed through the computed tomography scanner, the computed tomography scanner comprising: a gantry having an opening; and an x-ray source configured to project a fan beam of x-rays towards a detector array disposed on an opposite side of the gantry opening, wherein at least the x-ray source is mounted for rotation about the opening; a motorized conveyor for passing a plurality of objects through the opening; and a device positioned to detect the position of the conveyor for each position of the x-ray source as it rotates about the opening.

DETAILED DESCRIPTION OF EXEMPLARY EMBODIMENTS OF THE INVENTION

The disclosure of the present invention relates to an apparatus and method for data acquisition of an object being scanned by a CT system, the apparatus and method providing a means for data acquisition when a conveyor belt of the system is stopped or operated at various speeds during a CT scanning cycle. A major advantage of this process over the prior process is that the prior process required constant belt movement and accordingly additional queuing conveyors as well as more space between each bag being scanned as the prior CT scanning devices were not configured to utilize data from variable speed conveyors. Moreover, and once the belt has stopped exemplary embodiments of the present invention are configured to prevent unnecessary accumulation of data as well as projecting an unnecessary amount of radiation onto the object being scanned. Therefore, exemplary embodiment of the present invention allow for data acquisition during various operational speeds of the conveyor.

In accordance with exemplary embodiments of the present invention a control system will have an encoder or servo controller or any other equivalent mechanism to determine the conveyor position while views of an object are captured (acquired data) from single x-ray source position as the x-ray source rotates about the object moving through the scanner at various speeds. The acquired data, the source position, and the conveyor position at which each view was acquired is provided to a reconstruction algorithm of the CT scanner. The distance of conveyor or object travel between views may be variable or zero. The reconstruction algorithm will utilize variable interpolation in order to faithfully reconstruct the data.

In accordance with exemplary embodiments of the present invention, the conveyor position is determined by an encoder that is attached to a conveyor drive or roller mechanism, which will report increments of rotations of an axle of the drive or roller mechanism in appropriate units, wherein those units are converted to a conveyor position. In addition, the speed of the conveyor is deduced by differentiating the position or time periods between each position. Alternatively, a servo controller is configured to produce trajectories for the conveyor and the commanded (e.g., predicted) position and speed is reported as a signal to a control algorithm and the reconstruction algorithm.

In addition, the control system will be configured to detect that the conveyor has stopped for more than one gantry rotation of the x-ray source, after which data is no longer stored. The control system will also be configured to determine when the belt starts moving again, after which subsequent data is stored. In an alternative implementation, the control system detects when the conveyor has stopped for one or more gantry rotations, and in this embodiment the control algorithm will direct the data acquisition system to overwrite the previously acquired redundant data (e.g., data corresponding to successive gantry rotations at a single conveyor position). In another alternative implementation, the x-ray source may be turned off while data is not being required (e.g., extended periods of belt shut down) wherein an apparatus and method for preventing the belt from moving until the x-ray tube has been turned on and stabilized is provided.

Exemplary embodiments allow for reduced overall length of the CT scanner and required conveyors as exemplary embodiments provide for data acquisition during various stages of conveyor speed, which is not found in current scanners. Thus, the scanner requires less room in a facility, thereby reducing overall installation costs. In addition, and since the device is able to scan objects at various speeds or stop and start situations, less space is required between the bags or objects as exemplary embodiments allow for scanning to stop and restart without having to back up the bag or remove and replace the bag. Therefore, more bags can be scanned per hour.

Accordingly, a technical effect or effects of exemplary embodiments of the present invention are directed to providing a method and apparatus for data acquisition of an object being scanned when the conveyor belt has been, slowed, stopped and restarted during a CT scanning cycle. A detailed description of an embodiment of the present invention is presented herein by way of exemplification and not limitation with reference to FIGS. 1-7.

The following U.S. Pat. Nos. 5,182,764; 5,367,552; 5,960,056; and 6,647,084, the contents each of which are incorporated herein by reference thereto, provide non-limiting examples of Computed Tomography (CT) Systems.

Figure 1:
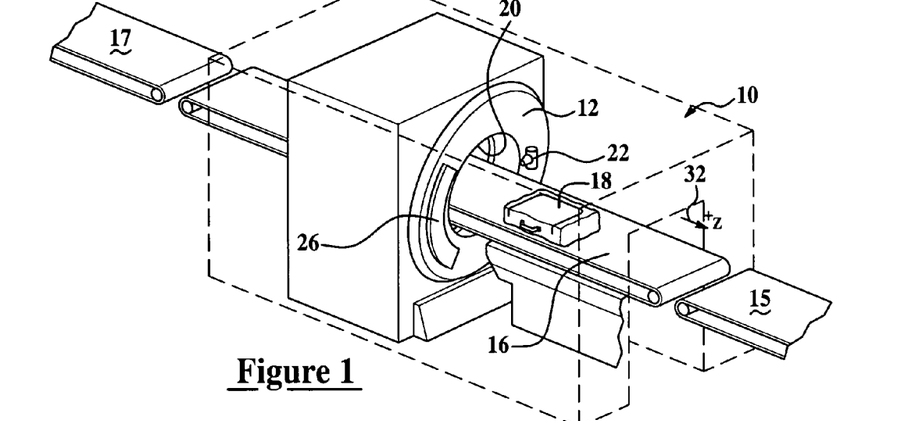
FIG. 1 is a schematic of a CT imaging system in accordance with an exemplary embodiment.
Figure 2:
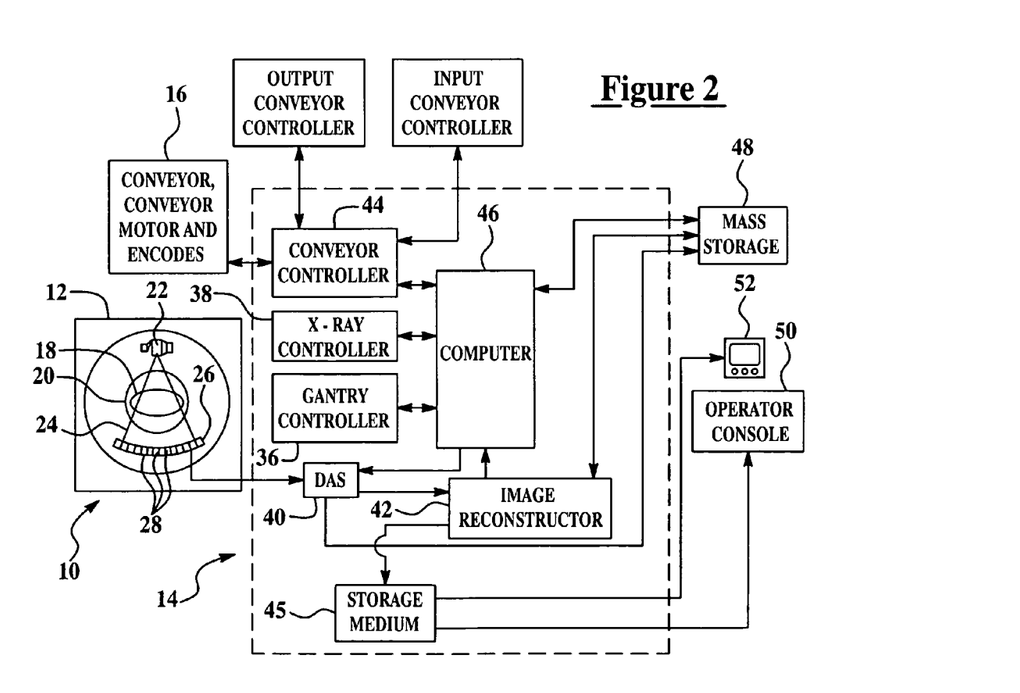
FIG. 2 is a block schematic of the CT imaging system of FIG. 1 in accordance with an exemplary embodiment of the present invention.

Referring now to FIGS. 1 and 2, a computed tomography (CT) imaging system 10 is shown. CT imaging system 10 is shown having a gantry 12, which is representative of a CT scanner, a control system 14, and a motorized conveyor belt 16 for passing an object 18, such as a piece of luggage, through an opening 20 in gantry 12. Gantry 12 includes an x-ray source 22 that projects a fan beam of x-rays 24 toward a detector array 26 on the opposite side of opening 20. Detector array 26 is formed by a plurality of detector elements 28, which are shown in more detail in FIG. 3 and discussed below.

Detector elements 28 are radiation detectors that each produce a signal having a magnitude that represents and is dependent on the intensity of the attenuated x-ray beam after it has passed through object 18 being imaged. During a helical scan that acquires x-ray projection data, the x-ray source and detector array rotate within a plane and around the object about a center of rotation, while the object is moved through the gantry in a z-direction 32 perpendicular to the plane of rotation. In accordance with an exemplary embodiment, and for most helical scanners the detector array will comprise a plurality of detector rings each having a plurality of detectors, the detector rings having an angular configuration corresponding to the x-ray source.

Gantry 12 and x-ray source 22 are controlled by control system 14, which includes a gantry controller 36, an x-ray controller 38, a data acquisition system (DAS) 40, an image reconstructor 42, a conveyor controller 44, a computer 46, a mass storage-system 48, an operator interface 50, and a display device 52. The gantry controller controls the rotational speed and position of the gantry, while the x-ray controller provides power and timing signals to the x-ray source, and the data acquisition system acquires analog data from the detector elements and converts the data to digital form and writes it to a storage medium 45 for subsequent processing. The image reconstructor receives the digitized x-ray data from the storage medium and performs an image reconstruction process that involves creating CT images from the projection data by using a helical reconstruction algorithm.

In accordance with one non-limiting embodiment, the DAS places scan data into the first mass storage device, and the image reconstructor reads data from the first mass storage device, reconstructs images, and places these reconstructed images in a second storage medium 48. The inspection system and the operator console receive will then receive images from the second storage medium 48.

In current practice it is common for the operator console to be separate from the machine itself wherein inspected images are written to a central server, and a set of operators inspect images from a set of machines.

Computer 46 is in operable communication with the gantry controller, the x-ray controller, and the conveyor controller whereby control signals are sent from the computer to the controllers and information is received from the controllers by the computer. The computer also provides commands and operational parameters to the data acquisition system and receives a reconstructed image data from the image reconstructor. The reconstructed image data is stored by the computer in the mass storage system 48 for subsequent retrieval. An operator interfaces with the computer through the operator interface, which may include, for example, a keyboard and a graphical pointing device, and receives output, such as, for example, a set of reconstructed images, annotations, and other information, on the display device. In accordance with an exemplary embodiment, computer 46 will receive signals from a scanning device in order to determine the distance an object has moved during one rotation of the x-ray source about the opening of the gantry.

Operable communication between the various system elements of FIG. 2 is depicted by arrowhead lines, which illustrate a means for either signal communication or mechanical operation, depending on the system element involved. Operable communication amongst and between the various system elements may be obtained through a hardwired or a wireless arrangement. The computer may be a standalone computer or a network computer and may include instructions in a variety of computer languages for use on a variety of computer platforms, such as, for example, PC, Apple or Sun Microsystems, and under a variety of operating systems, e.g. Windows, MacOS, and Unix or the like. Other examples of the computer include a system having a microprocessor, microcontroller or other equivalent processing device capable of executing commands of computer readable data or program for executing a control algorithm. In order to perform the prescribed functions and desired processing, as well as the computations therefore (e.g., the execution of image reconstruction algorithm(s), the control processes prescribed herein, and the like), the controller may include, but not be limited to, a processor(s), computer(s), memory, storage, register(s), timing, interrupt(s), communication interfaces, and input/output signal interfaces, as well as combinations comprising at least one of the foregoing. For example, the controller may include input signal filtering to enable accurate sampling and conversion or acquisitions of such signals from communications interfaces. As described above, exemplary embodiments of the present invention can be implemented through computer-implemented processes and apparatuses for practicing those processes.

As illustrated in FIG. 1, a CT system for checked baggage or carry-on items may be receiving objects, which need to be scanned, from an input conveyor belt 15 which provides an input to the system. After scanning the object, the scanner will deliver the objects to an output conveyor belt 17 which provides an output to the CT system. Moreover, the CT system itself will also have an independent conveyor 16 that operates in conjunction with the output and input conveyors. Most conveyor systems at airports have a series of conveyors each of which is configured to start, stop, slow down, and accelerate in conjunction with specific requirements of perhaps another single segment of the conveyor. For example, and when an output belt or slide of a single segment of a system is overloaded with luggage that has not been removed that segment and the conveying system will be slowed or stopped until the "log jam" is removed. Thereafter, the entire system will start up again by accelerating to a predetermined speed.

In one non-limiting exemplary embodiment, bags are received from a single input belt 15, which in turn receives bags from one or more conveyor lines and the scanner will output to a single conveyor 17, which may be followed by a diverter to direct a cleared bag to one conveyor and suspect bags to another. Once scanned and passed out onto conveyor 17 a device with a pusher (not shown) pushes the cleared bag off the conveyor 17 onto another output conveyor, while a suspect or uncleared bag continues straight onto yet another output conveyor.

In an exemplary embodiment, a primary conveyor 16 carries the bag or object through the scanner. As illustrated, conveyor 16 receives a plurality of bags from input conveyor 15, which received bags from multiple conveyors to deliver the bags to the scanner. Conveyor 16 receives a bag when conveyor controller 44 sends a signal to conveyor 15 controller that conveyor 16 is ready to receive a bag. In addition, output conveyor 17 or output conveyors will receive scanned bags from the scanner and cleared or un-cleared bags are diverted to an appropriate destination. For example and in a typical airport security screening cleared bags will go to the airport personnel for transport while uncleared bags will receive further inspection from another scanner and/or actual physical inspection. Similarly, conveyor controller 44 receives a signal from conveyor 17 controller when conveyor 17 can or cannot receive a bag. In one exemplary embodiment, it is this signal that forces conveyor 16 to stop if the scanned bags are not able to be received by conveyor 17.

Although an airport security screening process is described above, exemplary embodiments of the present invention are intended to be used with any transportation security screening process (e.g., trains, ships) as well as non-travel related security screening process, for example, security screening at public buildings (e.g., court houses or other building wherein security screening is desired).

Figure 3:
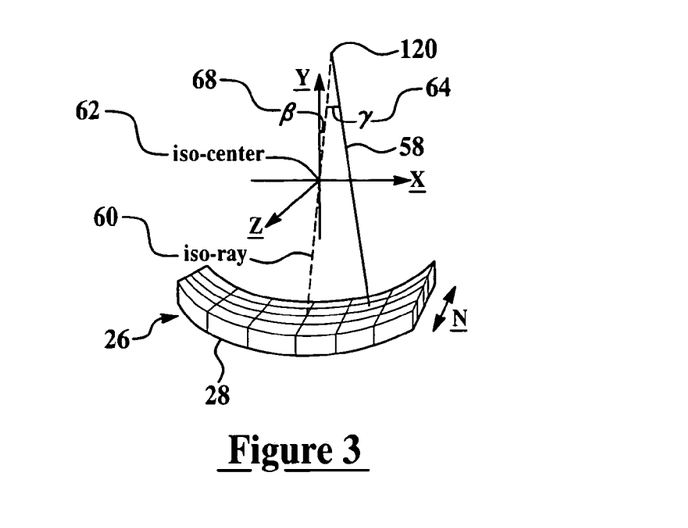
FIG. 3 is a schematic illustration of an x-ray beam and detector array.

Referring now to FIG. 3, an illustration of x-ray beam 58, having a beam axis (iso-ray) 60 that originates at the x-ray source and passes through center of rotation (iso-center) 62, relative to the detector array, having the detector elements arranged in rows n and columns m, is provided. While FIG. 3 depicts only four rows (n=4 for four rings) and six columns (m=6 for six detectors per ring), it will be appreciated that any number of rows and columns may be employed as a matter of design choice. In accordance with a non-limiting exemplary embodiment, n=32 rings and m=600 detectors. Moreover, and in other alternative exemplary embodiments, the detector array comprises a ring of detectors that surround the opening and only the x-ray source is rotated. As depicted in FIG. 3, a detector angle γ 64 is shown as an angle formed between detector cell m and the iso-ray which connects the x-ray source and the iso-center, and a projection angle β 68 is shown as an angle formed by the iso-ray with the y-axis.

Figure 4:
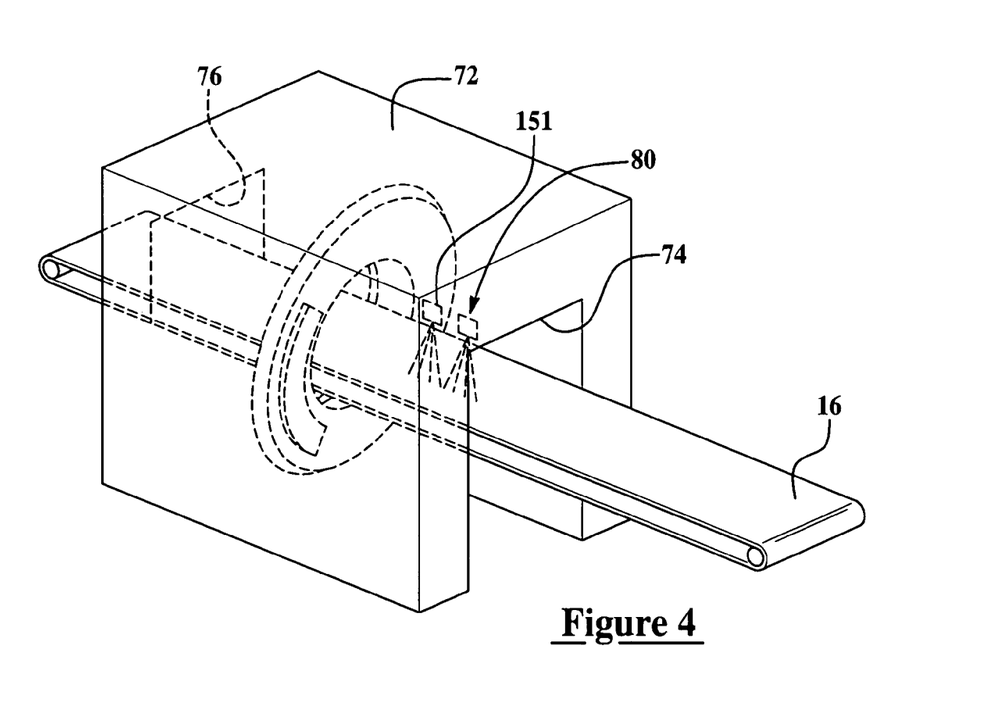
FIG. 4 is a schematic of a CT imaging system in accordance with an exemplary embodiment.

Referring now to FIG. 4, a perspective view of a CT scanning system in accordance with an exemplary embodiment of the present invention is illustrated. As illustrated, the CT scanning system has a structure 72 configured to contain therein at least a gantry of a CT scanner therein, wherein the gantry comprises an x-ray source that projects a fan beam of x-rays toward a detector array on the opposite side of the gantry. As previously discussed, a non-limiting example of one such gantry and CT scanner is illustrated in FIGS. 1 and 2, wherein the x-ray source and detector array rotate about the gantry opening.

In order to pass objects through the system, the structure is configured to have an input opening 74 and an outlet opening 76, each of which are configured to allow objects placed on a motorized conveyor belt 16 to pass into opening 74, through a gantry opening 20 for CT scanning and thereafter out outlet opening 76. Alternatively, the system may have the configuration of FIG. 1 (e.g., no exterior structure 72 used with gantry 12) as long as the necessary x-ray shielding is provided.

In accordance with an exemplary embodiment, a device for determining the conveyor position is provided in one exemplary embodiment, the device is either an encoder attached to the conveyor drive mechanism or a roller mechanism, which can provide the number of rotations of an axle in appropriate units for conversion to a conveyor position. Alternatively, both devices may be employed to provide a redundant signal indicative of conveyor position. Regardless of the type of conveyor position or encoder device employed, a signal indicative of the conveyor position will be sent to the computer. Of course, a single input or multiple inputs may be provided as necessary to determine the conveyor belt speed.

Figure 5:
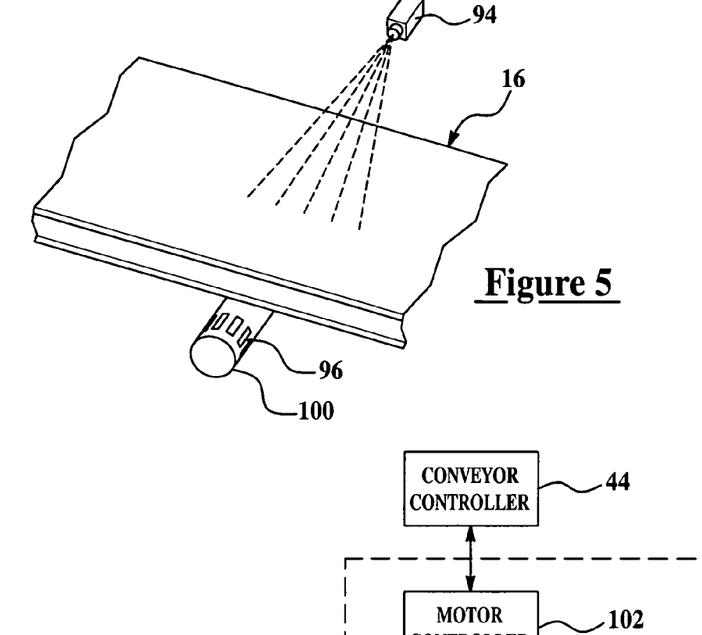
FIGS. 5-7 are partial schematic illustrations of conveyor position encoder in accordance with exemplary embodiments of the present invention.
Figure 6:
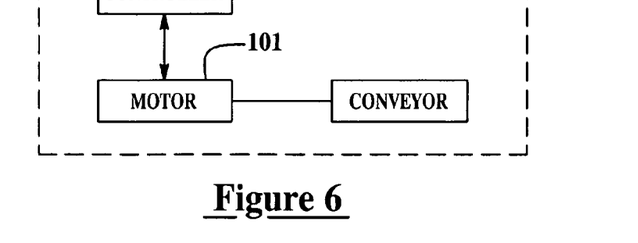
Figure 7:
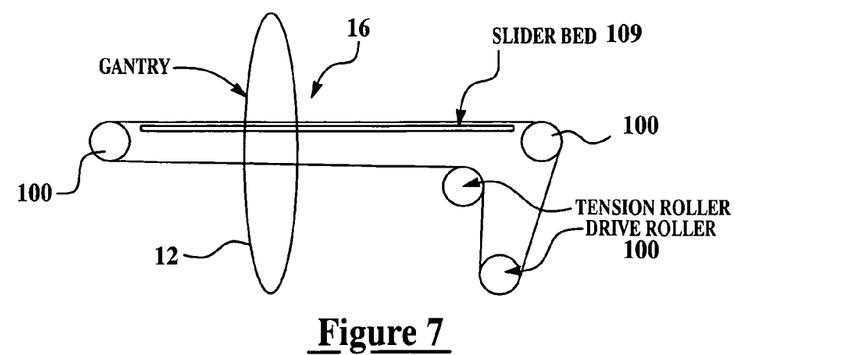

Non-limiting examples of such devices are illustrated in FIGS. 5-7. For example, in FIG. 5 a scanner 94 is positioned to detect machine readable code 96 disposed on roller 100. In one non-limiting example, the encoder may comprise a series of optically detected patterns 96 and the detector is configured to detect the presence or lack thereof. For example and when the scanning device is an encoder, the scanning device will comprise a light source, and a photodetector (e.g., light sensor), wherein alternating patterns of the machine readable code are detected. For example, and as the roller is rotated the alternating patterns of the machine readable code will interrupt the light reflected back to the photodetector wherein the photodetector will generate a digital or analog signal output. Alternatively and referring now to FIG. 6, conveyor 16 further comprises a motor 101 and motor controller or servo controller 102, wherein the servo controller is configured to produce trajectories for the conveyor and the commanded (e.g., predicted) position and speed is reported as a signal to a control algorithm of the control system, conveyor controller 44.

Referring now to FIG. 7, a schematic illustration of a typical conveyor belt is provided wherein a plurality of rollers are positioned to define a path of movement of the conveyor as well as provide tension and/or a driving force to the conveyor belt. In this Figure, the gantry is illustrated schematically and will of course have a width greater than that shown in the Figure. In addition, the conveyor system will also comprise a slider bed 109 disposed below a portion of the conveyor. As illustrated, the belt will form a bend around the rollers and the encoder could be on any one of the four rollers shown in FIG. 7, wherein a scanner is positioned to detect machine readable code disposed on a surface of the roller that extends past or is visible from the surface of the conveyer belt. As illustrated, the lower roller is a drive roller and the roller positioned between the drive roller and the slider bed is a tension roller. In an alternative exemplary embodiment, the system could use one of the end rollers as the drive roller, and the other end could be the tension roller.

Figure 8:
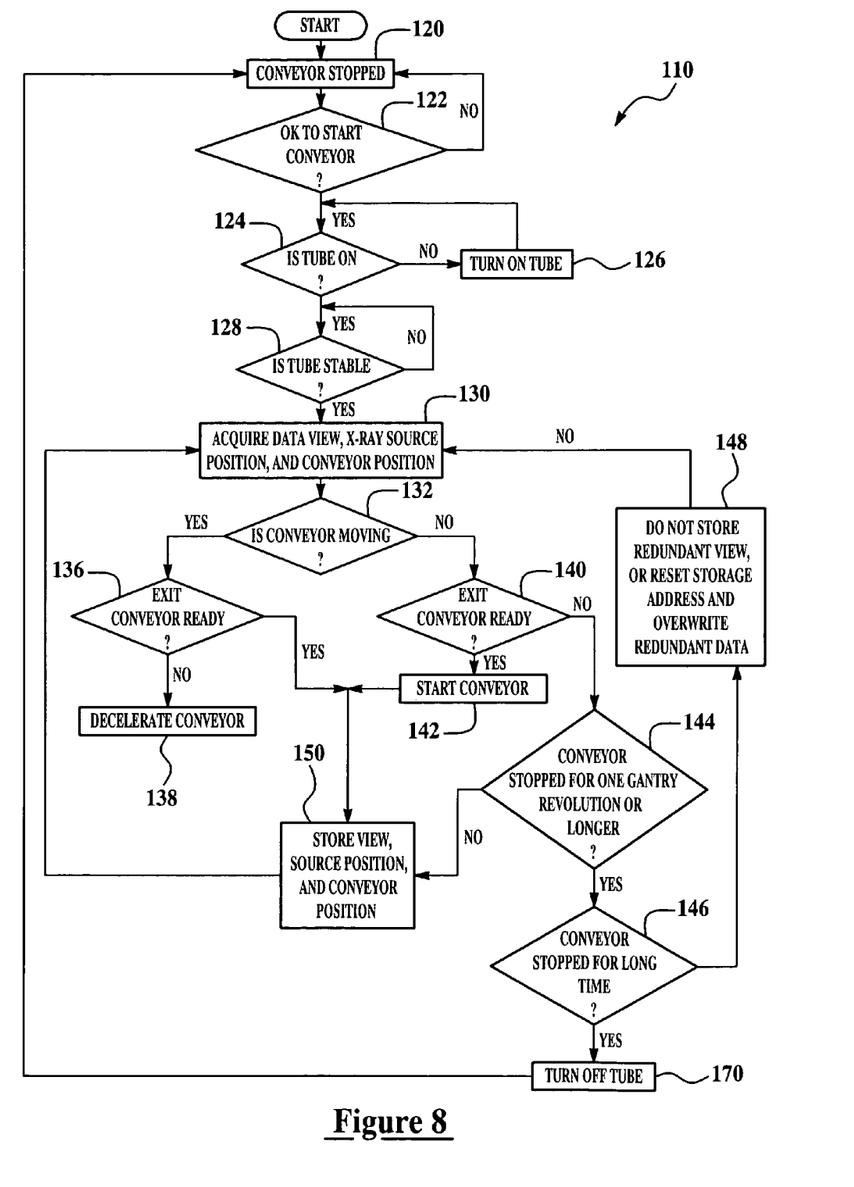
FIG. 8 is a flowchart illustrating portions of a control algorithm contemplated for use in exemplary embodiments of the present invention.

Referring now to FIG. 8, portions of a control algorithm 110 contemplated for use in exemplary embodiments of the present invention is illustrated. As discussed herein, it is desirable to input the conveyor belt position to a control algorithm of the CT scanning system, such that views from the x-ray source at the same gantry position will be able to accommodate or interpolate variations in the Z direction or direction corresponding to belt movement. Referring to step 120, the x-ray tube is off. At step 122, the system checks for a startup condition, for example, the operator requests a start, a bag arrives at the input conveyor after the system has been in idle, or the exit conveyor is ready to receive a bag that is in the scanner. These conditions may be provided by signals of conveyor 17 controller and conveyor 15 controller, if no startup conditions are met, the tube remains off. However, if a startup condition is met, at step 124 the system determines if the tube is on. If it is not, at step 126 the tube is turned on. If the tube is on, then at step 128 the system determines if the tube is stable (e.g. tube output monitor has been at desired level for a certain amount of time). The system remains at step 128 until the tube is stable.

Once the tube is stable at step 130, CT data for one view is acquired, along with the x-ray source position and conveyor position. At step 132, the system determines whether the conveyor is moving. Again this information is provided by an encoder positioned to detect conveyor or motor drive movement, if so, then at step 136 the status of the exit conveyor (conveyor 17) is determined. If the exit conveyor is no longer able to receive a new bag then the CT conveyor must be stopped, so at step 138 the conveyor controller is instructed to begin decelerating the conveyor. However, processing will continue at step 150.

If, at step 132, the conveyor was not moving, then at step 140 the status of the exit conveyor is checked to determine whether it is ready to receive a bag. If it is ready, the CT conveyor is instructed to start accelerating (box 142), and processing continues at step 150.

If, with the conveyor stopped at step 140, the exit conveyor is still unable to receive the bag, the conveyor remains stopped, and at step 144 the system determines whether the conveyor has been stopped for more than one complete revolution (e.g. the acquired data is redundant). If it has not, then processing proceeds to step 150. If at step 144 the conveyor has been stopped for more than one revolution (e.g. the acquired data is redundant), then at step 146 there is an optional test to determine if the conveyor has been stopped for a predetermined time after which the x-ray tube should be turned off (e.g., excessive radiation or over accumulation of redundant data). If so, the tube is turned off at step 170, and processing returns to step 120. If the tube is not to be turned off, then the data for the view is not stored (step 148), and processing returns to step 130. In an alternative embodiment, at step 148 the storage address for the view is reset to the location of the previously acquired redundant view, and the redundant view is overwritten by the new view. Thereafter, processing returns to step 130.

In yet another alternative exemplary embodiment and when a stopped conveyor position is detected during an object scan, the algorithm can be configured to either immediately shut off the x-ray source and thereafter require one complete revolution of the x-ray source about the object before allowing the conveyor to advance again or as discussed above one complete revolution is required before shutting the x-ray source down.

Referring now to step 150, the view data, along with the x-ray source position and conveyor position, are stored in storage medium 48 which will be accessed by the reconstruction algorithm and processing returns to step 130.

Figure 9:
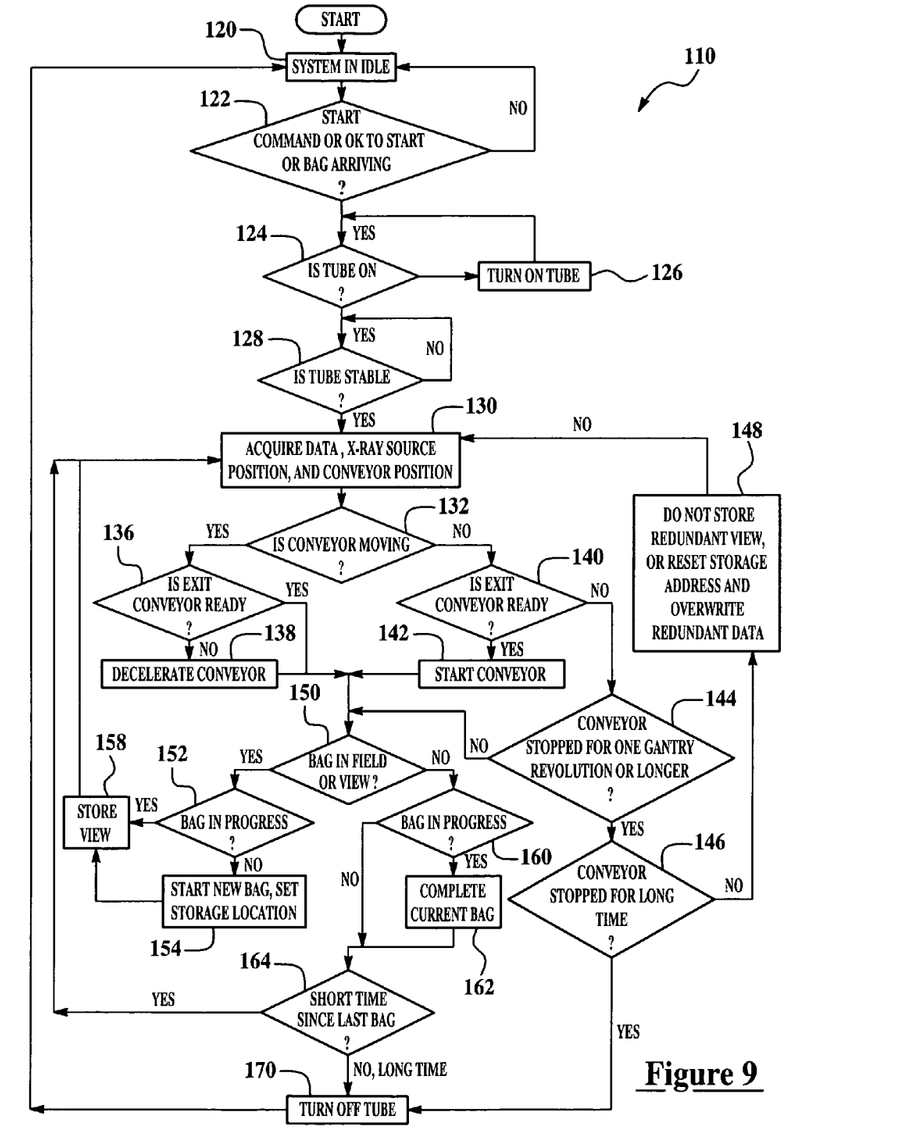
FIG. 9 is a flowchart illustrating portions of a control algorithm contemplated for use in an alternative exemplary embodiment of the present invention.

Referring now to FIG. 9, an alternative exemplary embodiment of the present invention is illustrated. In this embodiment step 150 is replaced by a decision node wherein it is determined whether there is a bag in the field of view of the CT scanning device. This may be accomplished by one of several means, for example, with the use of optical sensors or external control logic illustrated schematically as a scanner 151. If there is no bag in the field of view, then at step 160 it is determined if a bag is currently in process (e.g., data accumulated but not complete). If so, then at step 162 the bag is completed. If there was no bag in process at 160 or the bag is completed at 162, processing continues at step 164.

At step 164, if there has been only a short period of time since the last bag (e.g., predetermined time period of approximately 1 minute) was completed, processing returns to step 130. If it has been a long time with no activity (e.g., greater than predetermined time period), at step 170 the tube is turned off and the system returns to idle (box or step 120). Of course, exemplary embodiments of the present invention are intended to operate with predetermined time periods that are greater of less than one minute.

Accordingly, the system of exemplary embodiments of the present invention is capable of scanning objects at varying conveyor speeds. In addition, and since the system of various exemplary embodiments of the present invention allows for data acquisition during conveyor slowing, acceleration and stoppage, the objects are capable of being spaced closely together on the conveyor as there is no longer a need to have large buffer spaces between the objects or bags on the conveyor since prior art systems did not allow for data acquisition during conveyor, acceleration, deceleration or stoppage thus, the prior art systems required large gaps between the bags to allow for reacquisition of scan data corresponding to the objects being scanned. In other words, and in the prior systems and once the scanning of an object had began and if the conveyor had slowed or stopped, the prior systems were not configured to adapt for various conveyor speeds thus, data acquisition would have to start all over again. Therefore, the objects of the prior systems would have to be spaced appropriately apart thus allowing for the bags to be passed through or backed through the gantry opening after data acquisition ceases due to conveyor stoppage or speed variation.

In contrast, exemplary embodiments of the present invention allow for continuous data acquisition regardless of whether the conveyor is slowed, stopped or sped up again.

Accordingly, and in accordance with exemplary embodiments of the present invention, the scanning device operates in conjunction with or comprises an encoder or machine-readable code disposed proximate to the belt, and the apparatus provides a signal indicative of the belt position for each view of the x-ray source. In addition, the data acquisition hardware of the CT scanner system will be configured to recognize when the belt is stationary and a full rotation of data has been acquired. Thereafter, and after the belt has stopped moving the data acquisition hardware is configured to recognize when the belt starts moving again, and accordingly begin acquisition again by either stabilizing the x-ray source before allowing the belt to move or in the case of continuous x-ray source rotation during the conveyor stopped condition data acquisition begins with conveyor belt movement.

Accordingly, exemplary embodiments will input conveyor belt position into the control algorithm thus, the CT scanning system will be able to determine how much distance an object has traveled when acquired data from the next successive view from a discrete gantry location is determined, which may be greater or less than the amount the object traveled from the last view taken at that gantry position.

In particular, the methods of exemplary embodiments utilize a computer to monitor the conveyor belt operation as well as deactivating the accumulation of data when the conveyor belt has stopped and an object is located within the gantry. Therefore, data acquisition is continuous and each view of the object is tagged with the conveyor position at which it was taken.

As described herein, the apparatus and method of exemplary embodiments of the present invention provides a means for data acquisition when a conveyor belt of the system has been stopped or is operated at various speeds during a CT scanning cycle. Aspects of exemplary embodiments providing the desired technical effect can be embodied in the form of computer-implemented processes and apparatuses for practicing those processes. In an exemplary embodiment, the method is embodied in computer program code executed by one or more elements. The present method may be embodied in the form of computer program code containing instructions embodied in tangible media, such as floppy diskettes, CD-ROMs, hard drives, flash memory, or any other computer-readable storage medium, wherein, when the computer program code is loaded into and executed by a computer, the computer becomes an apparatus for practicing the invention. The present method can also be embodied in the form of computer program code, for example, whether stored in a storage medium, loaded into and/or executed by a computer.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A method of scanning an object with a CT scanner, the method comprising:
   acquiring an amount of data corresponding to the object that is scanned by the CT scanner using a radiation beam generated by an x-ray source at multiple x-ray source positions as the object passes through an opening in a gantry disposed about a conveyor for moving the object through the opening;
   monitoring a position of the conveyor as the object passes through the opening in the gantry;
   inputting the position of the conveyor at each x-ray source position into a reconstruction algorithm; and
   presenting a reconstructed CT image of the object, wherein stoppage of the conveyor during the scanning of the object will not require rescanning of a portion of the object already scanned prior to the stopping of the conveyor.

2. The method as in claim 1, further comprising a detector array on an opposite side of the gantry of the CT scanner from the x-ray source, wherein the detector array comprises a plurality of detector elements that are radiation detectors each being configured to produce a signal having a magnitude that represents and is dependent upon an intensity of an attenuated x-ray beam after it has passed through the object as the object is being passed through the gantry, the detector array being a multiple ring detector array and the object is intended for travel on an airplane.

3. The method as in claim 1, wherein the position of the conveyor and the x-ray source is provided to a control algorithm of the CT scanner, wherein the control algorithm is configured to determine when the x-ray source has completed one complete rotation with the conveyor at a single position.

4. The method as in claim 3, wherein the position of the conveyor is provided by an encoder that is configured to detect a position of the conveyor.

5. The method as in claim 3, further comprising:
   ignoring data acquired when the conveyor position has not changed and the x-ray source has completed one complete rotation with the conveyor at a single position.

6. The method as in claim 5, further comprising:
   determining if the conveyor position has not changed for a predetermined time period; and
   turning off the x-ray source if the conveyor position has not changed for a time period greater than the predetermined time period.

7. The method as in claim 6, further comprising:
   determining if a conveyor restart condition has occurred;
   turning the x-ray source on; and
   stabilizing the x-ray source before allowing the conveyor to move and data acquisition to occur.

8. The method as in claim 7, further comprising:
   determining if an object is in a field of view of the CT scanner when a conveyor stop signal is received from an output conveyor associated with the CT scanner; and
   completing a scan of the object before stopping the conveyor of the CT scanner.

9. The method as in claim 7, further comprising:
   determining if an object is being scanned by the CT scanner when a conveyor stop signal is received from an output conveyor associated with the CT scanner; and completing a scan of the object before stopping the conveyor of the CT scanner.

10. The method as in claim 3, further comprising:
receiving an output conveyor signal indicative of an operational status of an output conveyor configured to receive objects after they have been scanned by the CT scanner; and
receiving an input conveyor signal indicative of an operational status of an input conveyor configured to provide objects to the conveyor of the CT scanner.

11. The method as in claim 3, further comprising:
determining if the conveyor has been stopped; and
turning off the x-ray source when the conveyor is stopped for more than one gantry rotation.

12. The method as in claim 3, further comprising:
determining if the conveyor has been stopped;
turning off the x-ray source when the conveyor is stopped;
turning the x-ray source back on when a conveyor start condition has been detected;
rotating the x-ray source about the object for one gantry rotation; and
moving the conveyor after the x-ray source has been rotated about the object.

13. The method as in claim 1, further comprising:
determining if the conveyor has been stopped;
rotating the x-ray source about the object for one complete revolution after the conveyor has stopped; and
turning off the x-ray source after the one complete revolution.

14. The method as in claim 13, further comprising:
determining if a conveyor restart condition has been detected;
turning on the x-ray source; and
advancing the conveyor after the x-ray source has been turned on.

15. The method as in claim 14, wherein the x-ray source is rotated about the object as it is passed through the opening in the gantry and a detector array configured to receive the radiation beam comprises a ring of detectors surrounding the opening in the gantry and the ring of detectors remains stationary as the object is scanned by the CT scanner.

16. The method as in claim 14, wherein the CT scanner receives objects to be scanned from a plurality of input conveyors and scanned objects arc received by a plurality of output conveyors, wherein deceleration, acceleration and stopping of any one of the plurality of input conveyors or output conveyors will cause a corresponding reaction in the speed of the conveyor.

17. The method as in claim 1, further comprising:
determining if the conveyor has been stopped;
rotating the x-ray source about the object for at least one complete revolution after the conveyor has stopped;
storing the data acquired from the at least one complete revolution after the conveyor has stopped; and
discarding data acquired after the at least one complete revolution until the conveyor begins moving again.

18. The method as in claim 1, farther comprising:
determining if the conveyor has been stopped;
rotating the x-ray source about the object for at least one complete revolution after the conveyor has stopped; and
disregarding the data acquired from the at least one complete revolution after the conveyor has stopped.

19. The method as in claim 18, wherein the step of determining if the conveyor has stopped further comprises, reading machine readable data disposed on a surface of a roller of the conveyor by directing a scanning device towards a discrete area of a path of travel of the conveyor and wherein the disregarded data is stored in a storage medium.

20. A storage medium encoded with a machine-readable computer program code, the storage medium including instructions for causing a computer to implement a method comprising:
acquiring an amount of data corresponding to an object that is scanned by a CT scanner using a radiation beam generated by an x-ray source at multiple x-ray source positions as the object passes though an opening in a gantry disposed about a conveyor for moving the object though the opening;
monitoring a position of the conveyor as the object passes though the opening in the gantry;
inputting the position of the conveyor at each x-ray source position into a reconstruction algorithm; and
presenting a reconstructed CT image of the object, wherein stoppage of the conveyor during the scanning of the object will not require rescanning of a portion of the object already scanned prior to the stopping of the conveyor.

21. The storage medium as in claim 20, wherein the conveyor position is determined by an encoder in operable communication with a drive mechanism of the conveyor.

22. The storage medium as in claim 20, wherein the conveyor position is determined by a scanning device positioned to detect machine readable code disposed on a roller of the conveyor.

23. The storage medium as in claim 20, wherein the CT scanner receives objects to be scanned from a plurality of input conveyors and scanned objects are received by a plurality of output conveyors, wherein deceleration, acceleration and stopping of any one of the plurality of input conveyors or output conveyors will cause a corresponding reaction in the speed of the conveyor.

24. The storage medium as in claim 23, wherein the plurality of input conveyors and the plurality of output conveyors are portions of an airport security system and the object is intended for travel on an airplane.

25. A computed tomography system for providing an image of an object scanned by the system, the system comprising:
a CT scanner, configured to produce x-ray projection data as the object is passed through the CT scanner on a conveyor belt, said CT scanner comprising:
a gantry comprising an opening extending therethrough;
a conveyor configured to move the object through said opening;
an x-ray source coupled to said gantry; and
a detector array coupled to said gantry opposite said x-ray source; and
a control system operatively coupled to said CT scanner, said control system configured to:
acquire an amount of data corresponding to the object that is scanned by said CT scanner, wherein the amount of data is generated by said x-ray source projecting a radiation beam of x-rays toward said detector array, the radiation beam being generated at multiple x-ray source positions as the object passes through said opening;
monitoring monitor a position of said conveyor as the object passes through said opening;
input the position of said conveyor at each x-ray source position into a reconstruction algorithm; and
present a reconstructed CT image of the object, wherein stoppage of said conveyor during scanning of the object will not require rescanning of a portion of the object already scanned prior to the stopping of said conveyor.

26. The system as in claim 25, wherein said control system is further configured to:
- receive a position of said conveyor and x-ray source at which the amount of data is acquired from an encoder that is configured to detect the position of said conveyor;
- provide the position to a control algorithm of said CT scanner; and
- determine when said x-ray source has completed one complete rotation with said conveyor at a single position using the control algorithm.

27. The system as in claim 26, wherein said control system is further configured to:
- ignore data acquired when a conveyor position has not changed and said x-ray source has completed one complete rotation with the conveyor at a single position;
- determine if the conveyor position has not changed for a predetermined time period;
- turn off the x-ray source if the conveyor position has not changed for a time period greater than the predetermined time period;
- determine if a conveyor restart condition has occurred;
- turn said x-ray source on; and
- stabilize said x-ray source before allowing said conveyor to move and data acquisition to occur.

28. The system as in claim 26, wherein said control system is further configured to:
- determine if said conveyor has been stopped;
- rotate said x-ray source about the object for one complete revolution after said conveyor has stopped;
- turn off said x-ray source after the one complete revolution;
- determine if a conveyor restart condition has been detected;
- turn on said x-ray source; and
- advance said conveyor after said x-ray source has been turned on.

29. The system as in claim 28, wherein said CT scanner receives objects to be scanned from a plurality of input conveyors and scanned objects are received by a plurality of output conveyors, wherein deceleration, acceleration and stopping of any one of said plurality of input conveyors or output conveyors will cause a corresponding reaction in the speed of said conveyor and the object is intended for travel on an airplane.

30. A computed tomography system for scanning items, the system comprising:
- a computed tomography scanner configured to produce x-ray projection data as an object is passed through the computed tomography scanner, the computed tomography scanner comprising:
  - a gantry having an opening; and
  - an x-ray source configured to project a beam of x-rays, wherein the
- x-ray source is mounted for rotation about the opening;
- a motorized conveyor for passing a plurality of objects through the opening; and
- a scanning device positioned to detect a position of the conveyor, wherein the scanning device provides the position into a control algorithm of the CT scanning system wherein the control algorithm is configured to determine a distance the object has traveled in the gantry opening, the distance corresponding to one complete revolution of the x-ray source about the gantry opening, wherein stoppage of the conveyor during the scanning of the object will not require rescanning of a portion of the object already scanned prior to the stopping of the conveyor and the plurality of input conveyors.

31. The computed tomography system as in claim 30, wherein the computed tomography scanning device rotates the x-ray source about the object for one complete revolution after the conveyor has stopped and the x-ray source is shut down after one complete revolution and the CT scanner receives objects to be scanned from a plurality of input conveyors and scanned objects are received by a plurality of output conveyors, wherein deceleration, acceleration and stopping of any one of the plurality of input conveyors or output conveyors will cause a corresponding reaction in the speed of the motorized conveyor.

* * * * *